United States Patent [19]
Phillips

[11] Patent Number: 5,427,091
[45] Date of Patent: Jun. 27, 1995

[54] PNEUMATIC COMPRESSOR FOR BAG-VALVE-MASK RESUSCITATORS

[76] Inventor: Paul V. Phillips, 1337 Mill Street, North Vancouver, B.C., Canada, V7K 1V5

[21] Appl. No.: 120,265

[22] Filed: Sep. 13, 1993

Related U.S. Application Data

[63] Continuation-in-part of Ser. No. 18,443, Feb. 16, 1993, abandoned.

[51] Int. Cl.$^6$ .................... A62B 7/00; A61M 16/00
[52] U.S. Cl. .................... 128/205.15; 128/205.13; 128/202.28; 128/202.29
[58] Field of Search ............ 128/200.24, 202.28, 128/202.29, 203.11, 203.28, 204.18, 205.13, 205.15, 205.17

[56] References Cited

U.S. PATENT DOCUMENTS

| | | | |
|---|---|---|---|
| 2,119,446 | 5/1938 | Sholes | 128/203.13 |
| 2,284,964 | 6/1942 | Mautz et al. | 128/205.15 |
| 2,970,749 | 2/1961 | Montague | 128/205.13 |
| 3,046,978 | 7/1962 | Lea | 128/205.13 |
| 3,090,380 | 5/1963 | Dold | 128/205.13 |
| 3,291,121 | 12/1966 | Vizneau | 128/205.15 |
| 3,467,092 | 9/1969 | Bird et al. | 128/205.15 |
| 3,650,268 | 3/1972 | Ruben | 128/205.13 |
| 3,741,250 | 6/1973 | Mercier | 138/30 |
| 4,409,977 | 10/1983 | Bisera et al. | 128/205.15 |
| 4,821,712 | 4/1989 | Gossett | 128/205.15 |
| 4,883,051 | 11/1989 | Westenkow et al. | 128/205.15 |
| 5,067,487 | 11/1991 | Bauman | 128/205.13 |
| 5,140,982 | 8/1992 | Bauman | 128/205.13 |
| 5,163,424 | 11/1992 | Kohnke | 128/205.13 |
| 5,217,006 | 6/1993 | McCulloch | 128/205.13 |
| 5,222,491 | 6/1993 | Thomas | 128/205.13 |

FOREIGN PATENT DOCUMENTS

| | | | |
|---|---|---|---|
| 646890 | 8/1962 | Canada | 128/202.29 |
| 1207372 | 2/1960 | France | 128/202.29 |
| 1199929 | 9/1965 | Germany | 128/202.28 |

*Primary Examiner*—Kimberly L. Asher
*Attorney, Agent, or Firm*—Townsend and Townsend Khourie and Crew

[57] ABSTRACT

A pneumatic compressor is provided for bag-valve-mask resuscitators which permit a bladder to be compressed. The compressor permits resuscitators to be operated in the normal manner by squeezing, and also allows operation by blowing into a mouthpiece. A flexible enclosure can be easily installed over a flexible bag-valve-mask or a resuscitator, the enclosure has a plastic sleeve that can be fitted over the bladder and provides a sealed enclosure, and a tube is attached to an opening in the plastic sleeve, the tube has a mouthpiece at an exterior end to permit the enclosure to be pressurized and the bladder compressed.

11 Claims, 2 Drawing Sheets

PNEUMATIC COMPRESSOR FOR BAG-VALVE-MASK RESUSCITATORS

This application is a continuation-in-part of application Ser. No. 08/018,443 filed Feb. 16, 1993, now abandoned.

TECHNICAL FIELD

The present invention relates to bag-valve-mask resuscitators. More specifically the present invention relates to a pneumatic compressor for installing over a bladder portion of bag-valve-mask resuscitators permitting an operator to collapse or compress the bladder by pressurizing the enclosure.

BACKGROUND OF THE INVENTION

Hand held bag-valve-mask resuscitators are used by trained first aid or medical personnel to supplement breathing when respiratory activity in a patient is impaired or absent. Pocket masks are also used to resuscitate patients. Pocket masks fit directly over a patient's face, covering the nose and mouth, and have a mouthpiece for an operator to breathe into. Such a device allows the operator to perform artificial ventilation on a patient and in some cases a supplemental oxygen feed line is applied to feed oxygen to the patient. The pocket mask is held in place with two hands, ensuring an effective seal. There is direct lung to lung transfer of air between the operator and patient and this transfer of air directly from the lungs of the operator to those of the patient provides an avenue of infection. Furthermore, the pocket mask provides a lower concentration of supplemental oxygen than is possible with a bag-valve-mask resuscitator because the exhaled air from the operator mixes with the supplemental oxygen.

Bag-valve-masks presently used today have a squeezable bladder connected to a face mask covering the nose and mouth of a patient. The bladder can have a supplemental oxygen feed line and also an oxygen reservoir. The bladder is squeezed by hand and this compression forces oxygen therein through the face mask into the lungs of a patient. Such a system does not permit the transfer of air directly from the lungs of an operator to those of a patient. The face mask has a purge valve therein which permits oxygen to be forced into the mouth/nose of a patient but does not permit air exhaled from a patient to pass through the face mask into the bladder. This exhaled air is vented through the purge valve to the atmosphere.

After being squeezed, the bladder is released and reforms allowing oxygen to refill the bladder from the oxygen reservoir and from the oxygen supply. If there is not sufficient oxygen present, then a flap valve is provided to permit air to be drawn into the bladder at the same time. All these types of resuscitators are provided with a pressure relief valve so that if the pressure from the oxygen supply should become too high, then it bleeds off into the atmosphere.

Properly used, bag-valve-mask resuscitators with supplement oxygen feed line and reservoir bag attached can move 800 millilitres or more of 100% oxygen into the patient during each compression cycle. The hand operation of the bag-valve-mask allows the operator to provide a wide range of frequencies of respiratory cycles according to the patient's needs and up to the point where the operator's hand tires.

For effective operation, however, the bag-valve-mask resuscitator requires two people to operate it, and the patient must be supine. An operator must maintain proper head and neck position to operate the bag-valve-mask and at the same time must also squeeze the bladder to supply oxygen to the patient's lungs. However, in order to maintain a seal of the face mask to the patient's face, two hands are nearly always required. Therefore, one operator is required to position and hold the face mask in place and at the same time maintain head and neck position of the patient, while the second operator is required to squeeze the bladder. Such a resuscitator is disclosed in U.S. Pat. No. 5,163,424 to Kohnke.

Another type of resuscitator is shown in U.S. Pat. No. 5,222,491 to Thomas which provides a bladder which may be collapsed by a mechanical mechanism.

Yet a further example of a resuscitative device is disclosed in U.S. Pat. No. 3,291,121 to Vizneau, wherein a bladder inside a bladder is provided. When the outside bladder is squeezed, oxygen in the bladder is forced into the mouth of a patient from the outside bladder through a first tube and at the same time the inside bladder is deflated, pushing air to the atmosphere. When the two bladders are released, the outside bladder fills up with oxygen or, indeed, may be filled up by being blown into by an operator. The inside bladder draws air exhaled from the patient along a second tube and is then expelled in the next squeezing cycle.

Another example of a resuscitator is shown in Canadian Patent No. 646,890, wherein a rigid container is provided having a flexible diaphragm therein sealed in the center. One side of the container is connected to a face mask and the other side of the container is connected to a mouthpiece for an operator to blow into. There is an oxygen supply for filling the side of the container to be expelled through the face mask into the lungs of a patient and when an operator blows through the mouthpiece, the diaphragm moves in the container forcing oxygen therein through the face mask into the patient's lungs. When the container is empty, then it is necessary to allow more oxygen to enter the container and the diaphragm moves back towards the operator's side. The system may work well, but can only work by blowing and does not have the ability of being able to be squeezed as no bladder is provided. The container is a rigid container.

DISCLOSURE OF INVENTION

It is an aim of the present invention to provide bag-valve-mask resuscitators which operate in a normal manner wherein a bladder can be squeezed to supplement breathing and also which has a flexible enclosure sealed to the bladder with a tube attached to the enclosure with a mouthpiece for an operator to breathe into and thereby compress the bladder. Thus, the resuscitators can be operated either by blowing or providing compressed air into the mouthpiece or by squeezing the enclosure with the bladder therein. This allows an operator to position the face mask over a patient's mouth and nose and hold it in position with two hands and then blow into the mouthpiece, pressurizing the enclosure and at the same time deflating or compressing the bladder.

It is a further aim of the present invention to provide a kit comprising a flexible enclosure with sealing strap or straps that fits over the bladder of bag-valve-mask resuscitators, and has a tube attached to the enclosure permitting an operator to blow into the enclosure, or provide air from a compressed air source to pressurize the enclosure and compress the bladder.

The present invention provides in bag-valve-mask resuscitators having a face mask for fitting over the nose and mouth of a patient, a flexible bag-valve-mask bladder connected to the face mask, and means for supplying oxygen or air to the bladder, the improvement comprising a flexible enclosure surrounding the bladder and substantially sealed therearound, and a tube attached to an opening in the flexible enclosure and having a mouthpiece at an exterior end of the tube for an operator to pressurize the enclosure and compress the bladder therein.

In another embodiment of the present invention there is provided a flexible enclosure for installation over a flexible bag-valve-mask bladder of a resuscitator, the flexible enclosure comprising a plastic sleeve for fitment over the bladder, having sealing means to attach to at least one end of the bladder and provide a substantially sealed enclosure, and a tube attached to an opening in the plastic sleeve, the tube having a mouthpiece at an exterior end to permit the flexible enclosure to be pressurized and the bladder compressed.

BRIEF DESCRIPTION OF DRAWINGS

In drawings which illustrate embodiments of the present invention.

MODES FOR CARRYING OUT THE INVENTION

Figure 1:
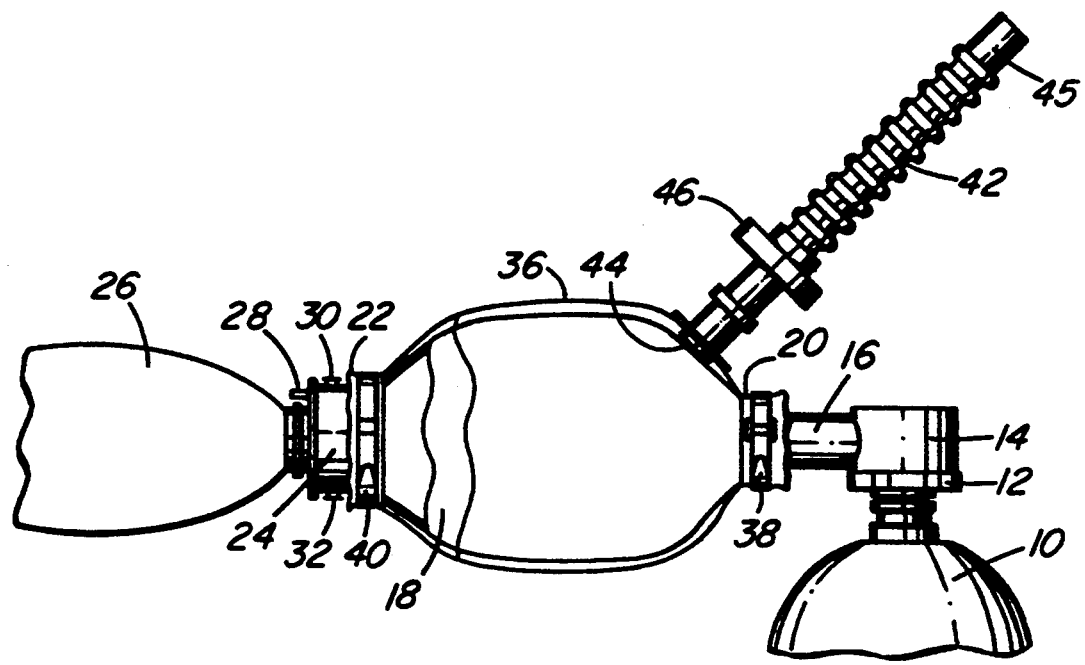
FIG. 1 is a side elevational view showing one embodiment of a flexible enclosure and tube fitted thereon installed on a bag-valve-mask resuscitator.
Figure 2:
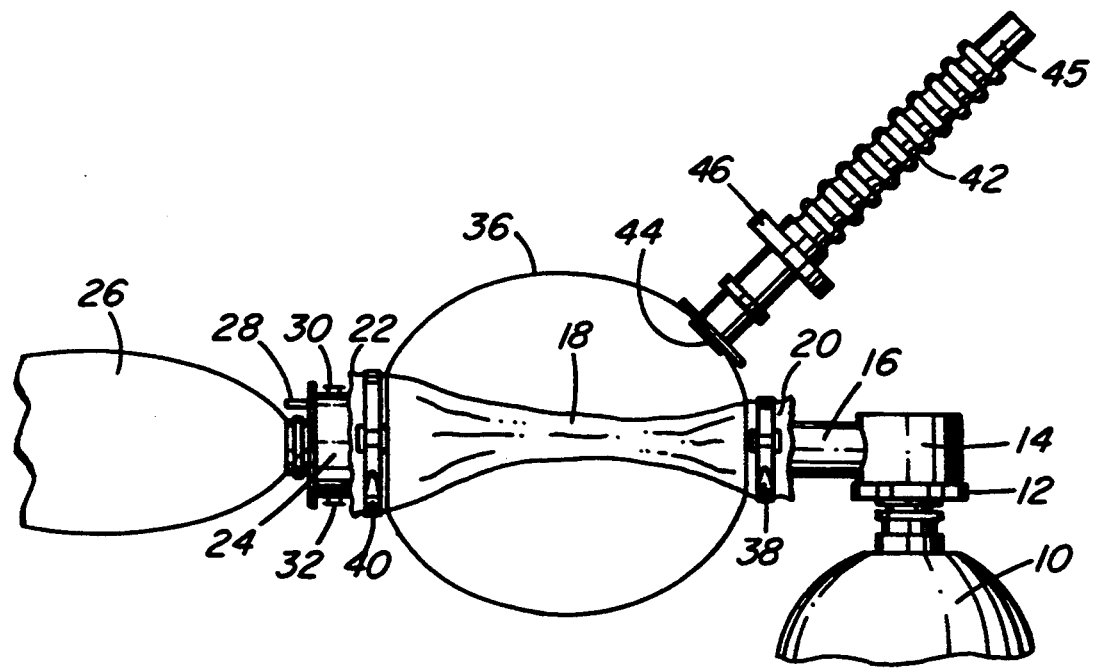
FIG. 2 is a side elevational view showing the resuscitator of FIG. 1 with the bladder compressed.

A bag-valve-mask resuscitator is shown in FIGS. 1 and 2 having a face mask 10 to fit over the nose and mouth of a patient. The face mask has a purge valve 12 whose details are not shown because they are well known. The purge valve allows oxygen or air to pass down through to the face mask 10 to a patient but does not permit air exhaled from the patient to return to the resuscitator. This exhaled air is vented to the environment at the purge valve 12. The face mask 10 is made of flexible polyethylene or other type of plastic material that can be adapted to fit over the nose and mouth of a patient and held in place to provide a good seal. The purge valve 12 joins to a short cylindrical body 14 which in turn has a tubular outlet pipe 16 extending to a squeezable bladder 18. An outlet collar 20, substantially rigid, is provided between the bladder 18 and the tubular outlet pipe 16. The bladder 18 is of a resilient material. After being squeezed or compressed to force air and oxygen out, the bladder returns to it's original form. An inlet collar 22 is provided at the other end of the bladder 18. This inlet collar 22 is substantially rigid and has included therein a flap valve (not shown) that permits air and oxygen to pass into the bladder 18, but prevents gas passing out through the inlet collar 22 when the bladder 18 is compressed or squeezed. A tubular insert member 24 fits within the collar 22 and is connected to a collapsible oxygen reservoir 26, preferably made of a plastic sheet material. There is also an oxygen supply inlet 28 joined to the insert member 24. The insert member 24 has a pressure relief valve 30 which prevents a build up of oxygen pressure in the oxygen reservoir 26 and the bladder 18. Oxygen bleeds out of the pressure relief valve 30 above a certain pressure. There is also a diaphragm valve 32 in the insert member 24. The diaphragm valve 32 permits air to be drawn into the bladder 18 when it reinflates itself if there is not sufficient oxygen present in the oxygen reservoir 26 and from the oxygen supply line 28. The bladder 18 is generally made of synthetic or natural rubber or plastic with resilient properties.

Figure 3:
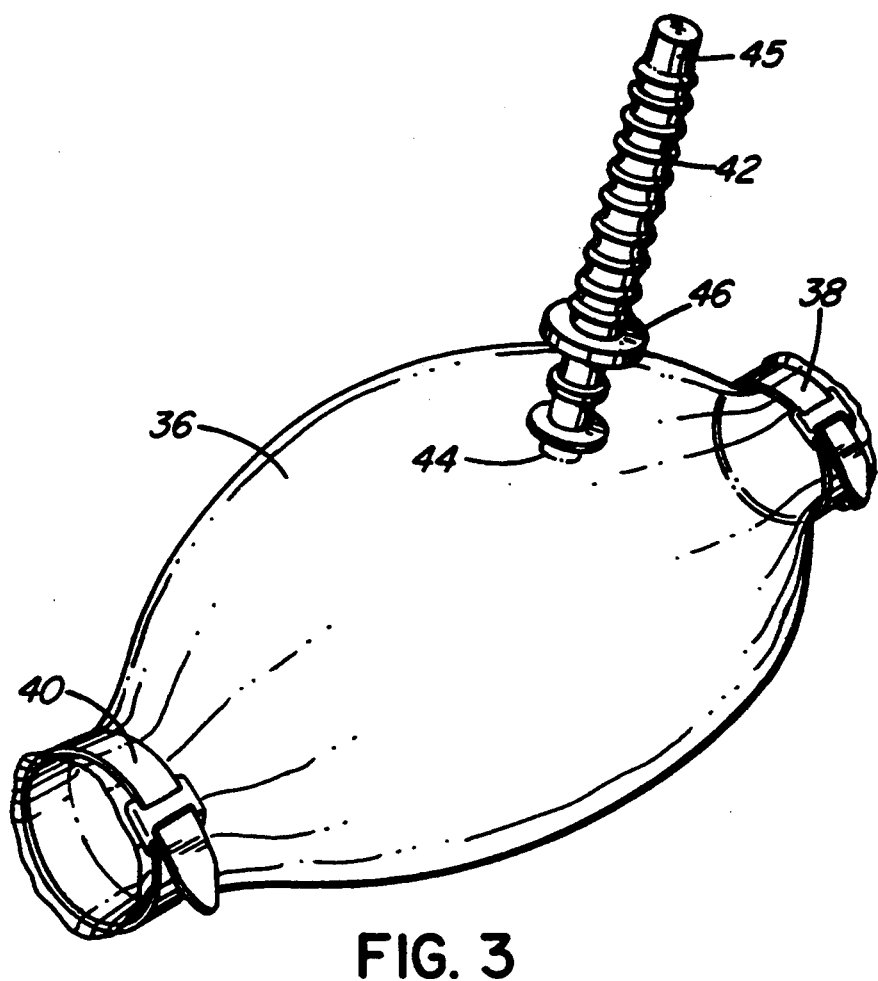
FIG. 3 is an isometric view of the flexible enclosure with a tube fitted thereon and two clamps for attaching the enclosure to the resuscitator.

A flexible enclosure 36, shown separately in FIG. 3, which is in the form of a sheet plastic tubular sleeve, fits over the bladder 18 and has a first strap 38 which reduces one end of the enclosure 36 and clamps it to the outlet collar 20. This provides a substantially sealed connection between the flexible enclosure 36 and the outlet collar 20. A second strap 40 reduces the other end of the flexible enclosure 36 and clamps it to the inlet collar 22 and seals it therearound. Thus, the bladder 18 is contained within a substantially sealed flexible enclosure. A flexible tube 42 connects to an aperture 44 in the flexible enclosure 36 and has a mouthpiece 45 at the exterior end for an operator to blow into the tube 42 and hence pressurize the flexible enclosure 36. At the bottom of the tube 42 is shown a purge valve 46 which is of the same type as purge valve 12 adjacent the face mask 10 and permits air to be blown into the enclosure 36 and prevents air from the enclosure 36 passing out through tube 42 to the mouthpiece 45. The air from the enclosure 36 is vented to the atmosphere at the purge valve 46.

FIG. 1 illustrates the bladder 18 in the full position being charged with oxygen. FIG. 2 illustrates the situation when an operator has blown through the tube 42, pressurized the flexible enclosure 36 and built up sufficient pressure in the enclosure 36 to deflate or compress the bladder 18. Thus, oxygen in the bladder 18 flows through the face mask 10 into the lungs of a patient. When an operator stops blowing into the mouthpiece 45 of the tube 42 and air within the enclosure 36 passes to the tube 42, if there is a purge valve 46 therein, the air vents to the atmosphere through the purge valve 46, then the bladder 18 reinflates to its original form with oxygen and/or air drawn in through the flap valve at the inlet collar 22.

The tube 42 of the flexible enclosure 18 is flexible to the extent that the mouthpiece 45 fits into an operator's mouth while the operator's hands are placed to hold the face mask 10 over the nose and mouth of a patient and ensure that it is sealed to the face of a patient. Then it is simply a matter of blowing into the tube 42 to compress or deflate the bladder 18, and then stop blowing and the bladder 18 reinflates. Thus, the resuscitator may be used by a single operator with two hands holding the face mask 10 to seal on the face of a patient. Another operator is not needed to squeeze the bladder 18 as this action is performed by pressurizing the flexible enclosure 36.

Whereas a mouthpiece 45 is illustrated in the drawings, this is merely shown as a tube end and in another embodiment a compressed air supply may be connected to the tube 42 to perform the same function as an operator blowing into the tube 42. A valve is needed on the compressed air supply to operate the breathing strokes of a patient.

Figure 4:
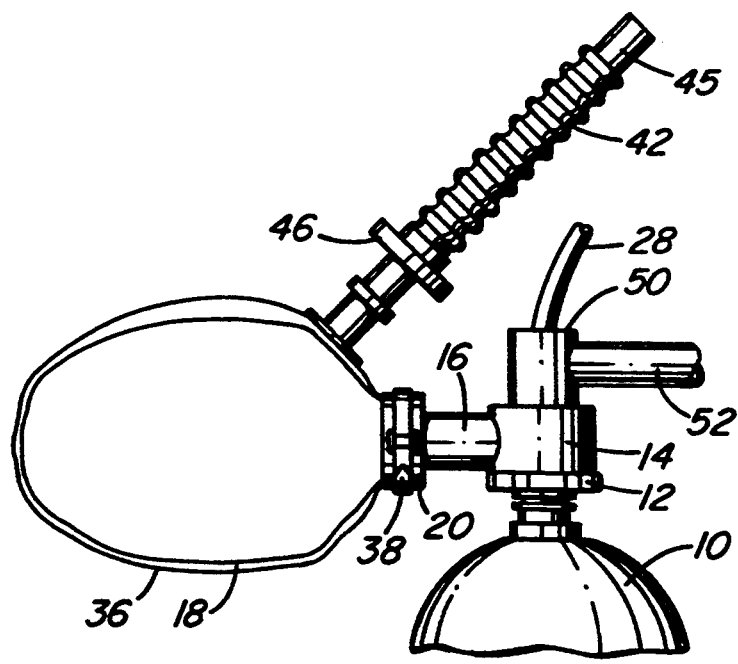
FIG. 4 is a side elevational view showing another embodiment of a flexible enclosure and tube fitted thereon installed on a bag-valve-mask resuscitator.

The flexible enclosure 36 and tube 42, together with the straps 38,40, form a kit as shown in FIG. 3, referred to as a pneumatic compressor, for attachment to different types of bag-valve-mask resuscitators and may be tailored to suit different types of resuscitators. Another type of resuscitator is illustrated in FIG. 4 wherein the bladder 18 has only one entrance and the outlet collar 20 joins the bladder 18 to the outlet pipe 16. Thus, the flexible enclosure 36 is in the form of a bag with a single strap 38 holding it and sealing it to the outlet collar 20. The resuscitator shown in FIG. 4 has an oxygen supply inlet 28 joined to an insert member 50 connected to the short cylindrical body 14 above the face mask 10. A reservoir connection 52 joins the insert member 50 to an oxygen reservoir (not shown). The resuscitator works in the same manner as that shown in FIGS. 1 and 2 and has the necessary valving therein to ensure that when the bladder 18 is squeezed or compressed oxygen therein passes through to the face mask 10 and when the bladder 18 is released and reinflates, oxygen enters the bladder 18 from the oxygen reservoir and the oxygen supply inlet 28.

The resuscitator including the pneumatic compressor, now permits a bag-valve-mask resuscitator to operate by two separate methods. In the first instance it can be used as a normal bag-valve-mask resuscitator by simply squeezing the bladder 18. This forces oxygen to the face mask 10 and into the lungs of a patient. Alternatively, it may be used by blowing into the mouthpiece 44 of the tube 42, or providing compressed air to the tube 42, thus pressurizing the flexible enclosure 36 and deflating or compressing the bladder 18. Should the enclosure 36 tear, it would still be possible to operate the bag-valve-mask resuscitator by squeezing the bladder 18.

The pneumatic compressor kit may be assembled very easily to a resuscitator without tools. The straps 38 and 40 are self-adhesive, generally having VELCRO (trade mark) fastenings. A rubber strip may first be wrapped around the collar on top of the plastic sheet for an improved seal. However, there are no tools needed for the installation of the pneumatic compressor kit and it may be easily attached or removed by an unskilled operator. Furthermore, once these kits have been attached to bag-valve-mask resuscitators, they may be collapsed and kept in a small container for ease of storage. They may be disposable units, in other words, after use the combination flexible enclosure 36 and tube 42 may be thrown out, or may be made of material that can be cleaned after use for reuse.

It is found that when the pneumatic compressor is used, the bladder 18 is capable of being deflated to 90 to 95% of its normal volume of oxygen or air therein, whereas when a bladder is squeezed by hand, it is generally only possible to deflate the bladder in a range of 30 to 60% depending partly on the size of a person's hand. Thus, a greater tidal air volume may be provided to the lungs of a patient by blowing through the mouthpiece 45 of the tube 42 to pressurize the flexible enclosure 36 and deflate or compress the bladder 18 than by squeezing the bladder 18.

The flexible enclosure 36 is preferably made of clear plastic sheet so that one is able to see the bladder 18 being collapsed.

Various changes may be made to the embodiments shown herein without departing from the scope of the present invention which is limited only by the following claims.

The embodiments of the present invention in which an exclusive property or privilege is claimed are defined as follows:

1. A flexible enclosure for installation over a flexible bag-valve-mask bladder of a resuscitator, the bladder having an outlet pipe at one end connecting to a face mask, and an insert member at an opposing end connecting to a gas inlet, the flexible enclosure comprising:
   a flexible plastic sleeve for fitment over the bladder;
   a first removable sealing collar to attach the sleeve to the outlet pipe of the bladder, and a second removable sealing collar to attach the sleeve to the insert member of the bladder said flexible plastic sleeve and said sealing collars providing substantially sealed enclosure, said sleeve have an opening and
   means for introducing gas into said flexible enclosure for pressurizing said flexible enclosure and for compressing the bladder, said means for introducing gas comprising a tube attached to said opening in the plastic sleeve, the tube having an inlet at an exterior end.

2. The flexible enclosure according to claim 1 wherein the plastic sleeve is transparent.

3. The flexible enclosure according to claim 1 wherein the sealing collars are removable straps.

4. The flexible enclosure according to claim 1 wherein the inlet at the exterior end of the tube has a connection for receiving gas supply.

5. The flexible enclosure according to claim 1 wherein the tube attached to the opening in the plastic sleeve has a purge valve therein, permitting gas to be blown through the tube into the sealed enclosure and permitting gas from the sealed enclosure to vent to atmosphere and not pass up the tube through the inlet.

6. A flexible enclosure for installation over a flexible bag-valve-mask bladder of a resuscitator, the bladder having an outlet pipe at one end connecting to a face mask and to a gas inlet, the flexible enclosure comprising:
   a flexible plastic bag for fitment over the bladder;
   a removable sealing collar to attach the plastic bag to the outlet pipe of the bladder said flexible plastic bag and said removable sealing collar providing a substantially sealed enclosure, an opening in said plastic bag;
   means for introducing gas into said flexible bag for pressurizing said flexible bag and for compressing the bladder, said means for introducing gas into said flexible bag comprising a tube attached to said opening in the plastic bag, the tube having an inlet at an exterior end.

7. The flexible enclosure according to claim 6 wherein the plastic sleeve is transparent.

8. The flexible enclosure according to claim 6 wherein the sealing collar is a removable strap.

9. The flexible enclosure according to claim 6 wherein the inlet at the exterior end of the tube has a connection for receiving a compressed gas supply.

10. The flexible enclosure according to claim 6 wherein the tube attached to the opening in the plastic bag has a purge valve therein, permitting gas to be blown through the tube into the sealed enclosure and permitting gas from the sealed enclosure to vent to atmosphere and not pass up the tube through the inlet.

11. The flexible enclosure according to claim 6 wherein the inlet at the exterior end of the tube is a mouthpiece.

* * * * *